United States Patent
Thiele

(10) Patent No.: US 7,771,354 B2
(45) Date of Patent: Aug. 10, 2010

(54) HIGH FRAME RATE THREE DIMENSIONAL ULTRASOUND IMAGER

(75) Inventor: Karl Thiele, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1089 days.

(21) Appl. No.: 10/544,143

(22) PCT Filed: Nov. 18, 2003

(86) PCT No.: PCT/IB03/05279

§ 371 (c)(1),
(2), (4) Date: Jul. 29, 2005

(87) PCT Pub. No.: WO2004/049952

PCT Pub. Date: Jun. 17, 2004

(65) Prior Publication Data

US 2006/0074310 A1   Apr. 6, 2006

Related U.S. Application Data

(60) Provisional application No. 60/430,876, filed on Dec. 4, 2002.

(51) Int. Cl.
*A61B 8/00* (2006.01)
*G06K 9/00* (2006.01)

(52) U.S. Cl. ...................... 600/437; 382/128
(58) Field of Classification Search ................ 600/437; 382/128
See application file for complete search history.

(56) References Cited

U.S. PATENT DOCUMENTS 6,263,093 B1 * 7/2001 Mochizuki ................. 382/128

FOREIGN PATENT DOCUMENTS

| EP | 0944026 | 9/1999 |
| EP | 1372001 | 12/2003 |

OTHER PUBLICATIONS

Basoglu, Chris et al "Computing requirements of Modern Medical Diagnostic Ultrasound Machines" Parallel Computing, vol. 24, 1998, pp. 1407-1431.

* cited by examiner

*Primary Examiner*—Eric F Winakur
*Assistant Examiner*—Michael T Rozanski

(57) ABSTRACT

A three dimensional ultrasound imaging device, having an interpolator that creates up sampled ultrasound image information from a three dimensional ultrasound image information using interpolation; and a memory that stores at least one of the three dimensional ultrasound image information and the up sampled ultrasound image information. The three dimensional ultrasound imaging device can have a probe that sends ultrasound waves, gathers reflected ultrasound waves and creates ultrasound information and a processor that converts the ultrasound information to three dimensional ultrasound image information. The ultrasound imaging device may also have a display that displays the up sampled image information. The three dimensional ultrasound imaging device may use at least one of 2 image to 3 image interpolation, 2 image to 4 image interpolation, 3 image to 4 image interpolation and 3 image to 5 image interpolation. The three dimensional ultrasound imaging device may use two dimensional solids and three dimensional volumes. The three dimensional ultrasound imaging device may also create up sampled ultrasound image information that has a greater number of frames, a greater number of three-dimensional frames, a greater number of two-dimensional volumes, a greater number of three dimensional volumes and a larger amount of ultrasound information.

18 Claims, 8 Drawing Sheets

HIGH FRAME RATE THREE DIMENSIONAL ULTRASOUND IMAGER

CROSS REFERENCE TO RELATED APPLICATION

This application claims the benefit of U.S. provisional application Ser. No. 60/430,876 filed Dec. 4, 2002, which is incorporated herein by reference.

BACKGROUND OF THE INVENTION

1. Field of the Invention

The present invention relates to an ultrasound device that produces a three-dimensional image.

2. Description of the Related Art

Ultrasound imaging devices operate by generating ultrasound signals and bouncing the ultrasound signals off an object to generate an image. The object may be a fetus or an internal organ such as a heart or kidney. FIG. 1 is a diagram illustrating a general system 100 for generating an ultrasound image. A patient 10 needing, for example, ultrasound image of their heart has a probe 20 placed against or near their chest. The probe 20 produces ultrasound signals and generates a volume of data from the received ultrasound signals. This data is sent to imager 50 that then produces an ultrasound image on display 90. The image may be saved for later review and/or may be transmitted to an external storage device.

A disadvantage of a conventional ultrasound system is that it is difficult to generate a three-dimensional image of sufficient size to either view the entire heart at once, or to have a frame rate high enough that the image does not appear jerky.

Several solutions have been proposed, such as increasing the processing power of the ultrasound device, reducing the overall area of the scanning such that the processing complexity drops and the scanning rate can be increased, image smoothing from frame to frame, and displaying only two-dimensional images.

However, all of these solutions suffer either extremely large size to produce the processing power or reduced diagnostic efficiency because of the small areas that are actually imaged.

SUMMARY OF THE INVENTION

An increased frame rate can be achieved at various stages in the ultrasound imaging process by using for example, interpolation to create three up sampled images using image data from two detected images. The up sampled imaged can then have a high frame rate without increasing the amount of scanning information gathered. The invention includes at least a three dimensional ultrasound device that creates up sampled images, the method of up sampling images for a three dimensional ultrasound image and a system for up sampling three dimensional ultrasound image information.

In one exemplary embodiment of the present invention linear interpolation/up sampling occurs in a three dimensional ultrasound diagnostic device after a three-dimensional volume has been rendered. The exemplary embodiment thus provides for an apparatus that includes a linear interpolator to an imaging device that also includes a beam former, detector, 3D scan converter and render engine.

The present invention also provides a method to increase the apparent frame rate in a three dimensional ultrasound diagnostic device, comprising receiving beams, organizing the beams in the planes, detecting 3D scan coordinate system objects, converting the 3D scan coordinate system objects to 3D volumes, interpolating to increase the number of volumes, rendering the 3D volumes for display and outputting the display information.

In various other exemplary embodiments, the interpolation to increase the number of volumes can occur at various stages in the process such as during the acquisition coordinate space; prior to detection of voxel to voxel; above but post detection (noncoherent); voxel to voxel after scan conversion (typically in Cartesian coordinates); and pixel to pixel after the volume has been rendered or the tomographic slice has been extracted from the full volume.

Thus, various exemplary embodiments up sample the number of volumes in a 3D xyz domain so that a viewer perceives an increased frame rate. The up sampling is advantageous in a three dimensional environment because of its computational simplicity and because coherent interpolation is likely to fail for a large number of cases, because the phase for given voxel from acquired volume is likely to be uncorrelated with its corresponding volume in voxel in the next volume.

Thus, exemplary embodiments of the invention include a three dimensional ultrasound imaging device, having an interpolator that creates up sampled ultrasound image information from a three dimensional ultrasound image information using interpolation and a memory that stores at least one of the three dimensional ultrasound image information and the up sampled ultrasound image information. The ultrasound imaging device may also include a probe that sends ultrasound waves, gathers reflected ultrasound waves and creates ultrasound information and a processor that converts the ultrasound information to three dimensional ultrasound image information. The ultrasound imaging device of may also have a display that displays the up sampled image information.

The ultrasound imaging device in several embodiments has the interpolation that is at least one of 2 image to 3 image interpolation, 2 image to 4 image interpolation, 3 image to 4 image interpolation and 3 image to 5 image interpolation. The ultrasound imaging device may act on three-dimensional information, two dimensional planes and three dimensional volumes. The ultrasound imaging device may also have the up sampled ultrasound image information that has at least one of a greater number of frames, a greater number of three-dimensional frames, a greater number of two-dimensional planes, a greater number of three dimensional volumes and a larger amount of ultrasound information.

BRIEF DESCRIPTION OF THE DRAWINGS

Advantages of the invention will become apparent and more readily appreciated for the following description of the preferred embodiments taken in conjunction with the accompanying drawings of which.

DETAILED DESCRIPTION OF THE INVENTION

Figure 1:
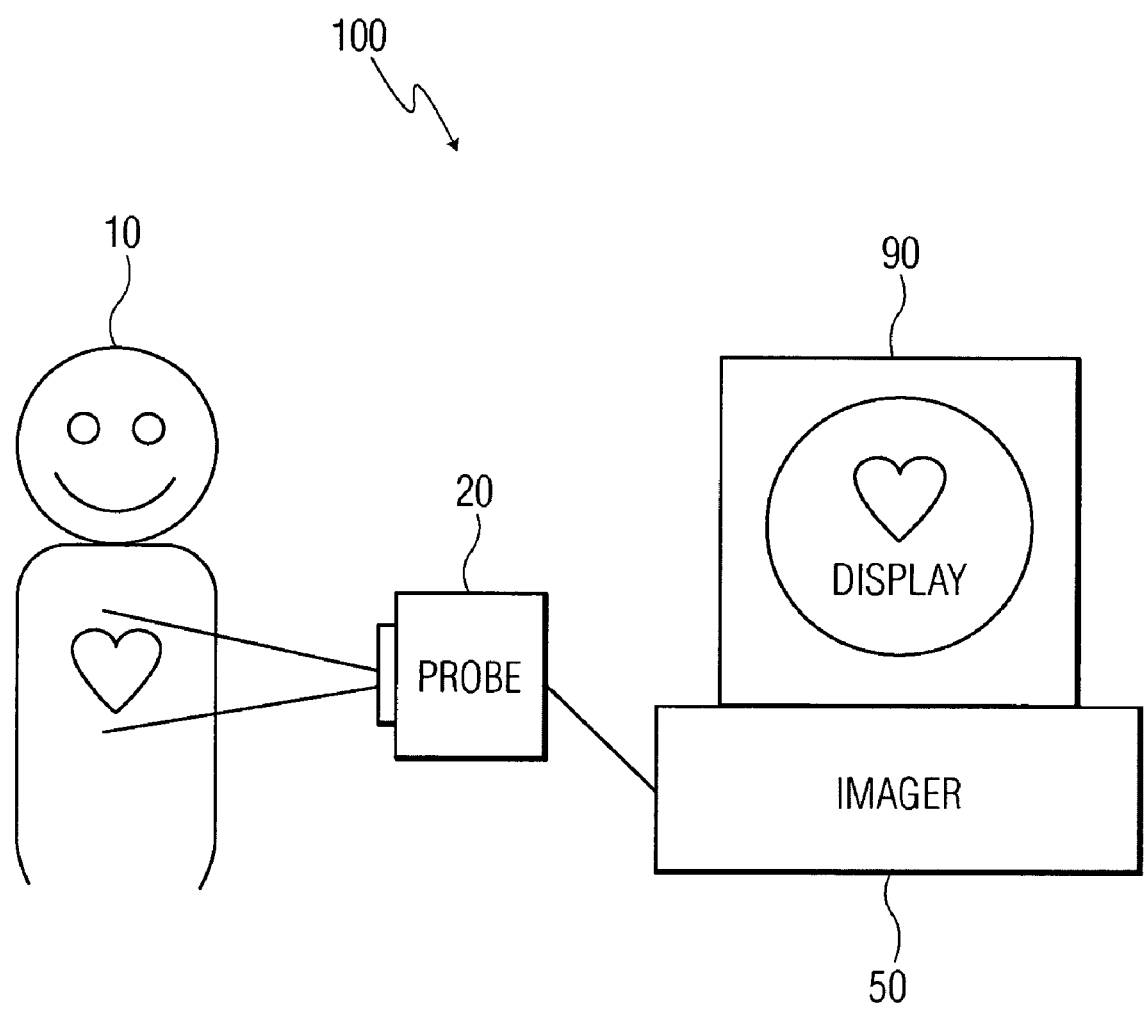
FIG. 1 illustrates a general ultrasound system.

Reference will now be made in detail to the exemplary embodiments of the present invention, examples of which are illustrated in the accompanying drawings, wherein like reference numerals refer to the like elements throughout.

The present invention creates a new, much higher frame frequency rate ultrasound device as can be seen in the general system diagram of FIG. 1. In FIG. 1, the patient 10 is having an ultrasound image taken of his heart using ultrasound system 100. Ultrasound system 100 includes probe 20, imager 50 and display 90.

The probe 20 emits ultrasound waves, which differentially bounce off a patient's heart and return to the probe 20. Ultrasound waves are reflected differentially depending on the density of an object. The probe 20 is connected to the imager 50. The imager 50 converts the data sent from the probe 20 of the ultrasound wave of the patient's 10 heart. The imager sends the data to the display 90. The display 90 can display an ultrasound image of the patient's heart.

Ultrasound waves are useful for many different applications, such as imaging hearts, fetuses and other portions of a human's anatomy. In addition, the system can be used to image any other material containing differential responses to ultrasound waves, such as metal, welds, or any other now know or later devised material.

Figure 2:
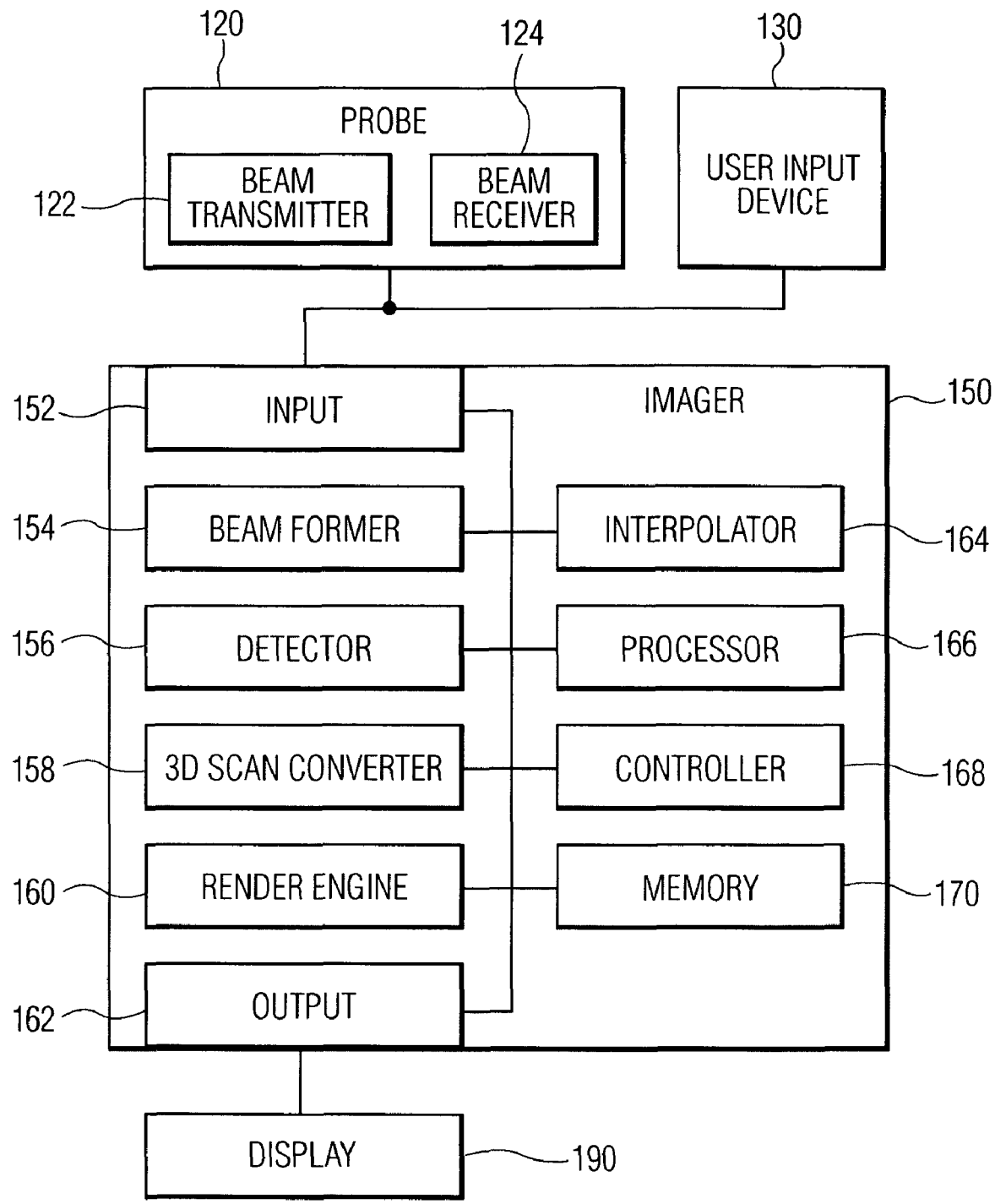
FIG. 2 is an exemplary ultrasound apparatus according to the invention.

FIG. 2 is an exemplary block diagram of an ultrasound-imaging device of the present invention. The ultrasound-imaging device has a probe 120, user input device 130, imager 150 and display 190. The probe 120 can contain a beam transmitter 122 and beam receiver 124. The beam transmitter 122 can be in a now known or later device apparatus for transmitting waves with a differential rate of reflection depending on the device to be inspected. The beam receiver 124 can be in a now known or later device that can receive the waves transmitted. The probe 120 can then translate the received information in the form of reflected waves and convert it into a transportable form for transmission to the imager 150.

User input device 130 can be a keyboard, a mouse, a light tablet or any other device for allowing the user to input and control the probe, the imager, or the display. Imager 150 can contain input 152, beam former 154, detector 156, 3D scan converter 158, render engine 160, output 162, interpolator 164, processor 166, controller 168, and memory 170. Imager 150 operates by receiving signals that correspond to the reflection of the waves received by the beam receiver 124 at input 152. The controller 168 can then direct the information to memory 170, interpolator 164 or beam former 154.

Other exemplary embodiments of three dimensional ultrasound devices can include additional modules, or combine several of the modules into one. For example, the beam former 154, detector 156, 3D scan converter 158, render engine 160 can be programs stored in memory 170 that are used to set a programmable processor 166 to perform the functions of beam former 154, detector 156, 3D scan converter 158 and render engine 160. Each of the beam former 154, detector 156, 3D scan converter 158, render engine 160 will be explained functionally in relation to a related three-dimensional ultrasound-imaging device.

A related three-dimensional ultrasound-imaging device uses standard processing steps. The first standardized processing step is to organize the received raw data into two-dimensional planes, called beam forming. The two-dimensional planes are then analyzed to detect 3D scan coordinates, called detecting. The 3D scan coordinates can then be aggregated to form 3D volumes, called 3D scan converting and the 3D volumes can then be rendered to be output on the display terminal.

The beam former 154 can thereby be used to form the beams into three-dimensional coordinates of information. The detector 156 can then be used to detect objects within the planes. The 3D scan converter 158 can then be used to convert the objects detected by detector 156 into three-dimensional objects. The render engine 160 can then be used to render the three-dimensional objects created by the 3D scan converter 158 into display data. The display data can then be output to output 162 and transferred to display 190 where the results are displayed.

3D scan coordinates can be a probe-centric coordinate system win which the data is stored in three dimensions related to the location of the probe. The three dimensions can be "r," the radial distance, sometime in Centimeters, from a body-target to a center of the probe face, "theta," the azimuth or lateral angel in degrees left or right from the center of the probe, and "phi," the elevation angle in degrees up or down from the center of the probe. 3D scan conversion can then be the converting the image information stored in 3D scan coordinates to another 3D data set, for example a Cartesian coordinate system, that can consist of X, Y and Z coordinates.

As noted above, beam former 154, detector 156, 3D scan converter 158, and render engine 160 can either be application specific integrated circuits, or programs to be implemented on processor 166. Controller 168 can control the flow of information from the input 152 to the output 162 and control the various steps in between. Memory 170 can be RAM, ROM, a hard drive or any other now known or later device means for storing data on either a temporary or permanent basis.

Interpolator 164 is a straight-line interpolator that forms one of many different types of average images from raw data. For example, a first frame of data may be entered into memory 170 and a second frame of data may be entered into memory 170. Interpolator 164 may then be used to create a third frame of data that is the average of the first two frames of data saved in memory 170. The interpolation can happen at any of several stages in the standardized process for creating a three-dimensional image.

The pre-scan coordinate system can vary as a function of various exemplary probe types used in various exemplary embodiments. A polar/spherical coordinate system is most applicable to a "sector" embodiment, which tends to scan the body using a windshield wiper fan sweep. An "Omni-Tee" probe is one exemplary embodiment of a probe using a cylindrical coordinate system. Other exemplary embodiments might scan the body using a parallelogram coordinate system.

Another exemplary embodiment of the invention can use a beam former that that scans in a spiral format, where the beams cannot be aligned along a traditional planar format. The invention is applicable regardless of the method of acquiring and analyzing the ultrasonic beams. Conversion can be used in various exemplary embodiments to facilitate "down stream" volume rendering. However, it is possible in other exemplary embodiments to render directly from raw, unconverted data sets.

A possible exemplary embodiment can take any 2 of the 3 polar dimensions and perform two dimensional scan conversion, resulting in a two dimensional plane of information for each value of the third dimension. The thereby created stack of two dimensional planes can then be three dimensionally converted to a three dimensional Cartesian coordinate system.

Figure 3:
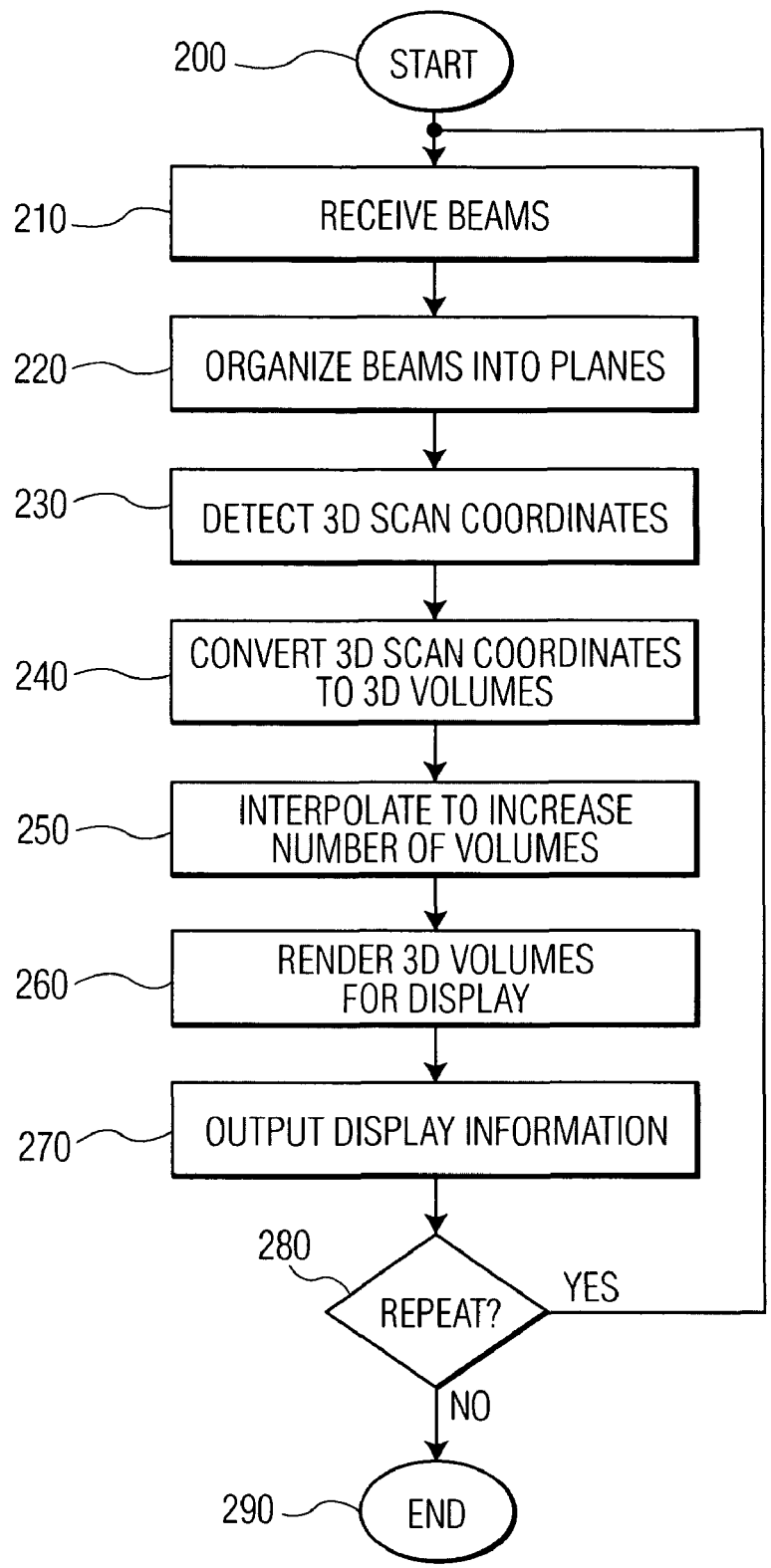
FIG. 3 is a flow chart illustrating a method of producing a high frame rate 3D ultrasound image according to the invention.

FIG. 3 is a flow chart of an exemplary process of applying the invention. The process starts at start 200 and continues to receive beams 210. In receive beams 210, reflected ultrasound frequency beams are received by the process as raw data. The method then continues to organize beams into planes 220.

Organize beams into planes 220 is where the raw data is organized into two-dimensional planes. The process then continues to detect 3D scan coordinates 230. In detect 3D scan coordinates 230, the planes of data are then analyzed to detect any 3D scan coordinates that may exist within the data. The process then continues to convert 3D scan coordinates to 3D volumes 240. In convert 3D scan coordinates to 3D volumes 240, the process organizes a series of 3D scan coordinates and converts them into 3D volumes. The process then continues to interpolate to increase the number of volumes 250.

In interpolate to increase the number of volumes 250, an interpolator can do a straight-line interpolation of the three-dimensional volumes across various iterations of the data in the time dimension. Thus, more three-dimensional volumes are created than were originally detected in the time realm. Thus, an increased frame rate can be displayed. The method then continues to render 3D volumes for display 260.

In render 3D volumes for display 260, the three-dimensional volumes are rendered for display on the display panel. The method then continues to output display information 270. An output display information 270, the render three-dimensional volumes are output to the display device. The method then continues to the determination of repeating 280. In determination of repeat 280, if the method is to continue the method jumps back to receive beams 210. If the method is to conclude the method continues to end 290.

Figure 4:
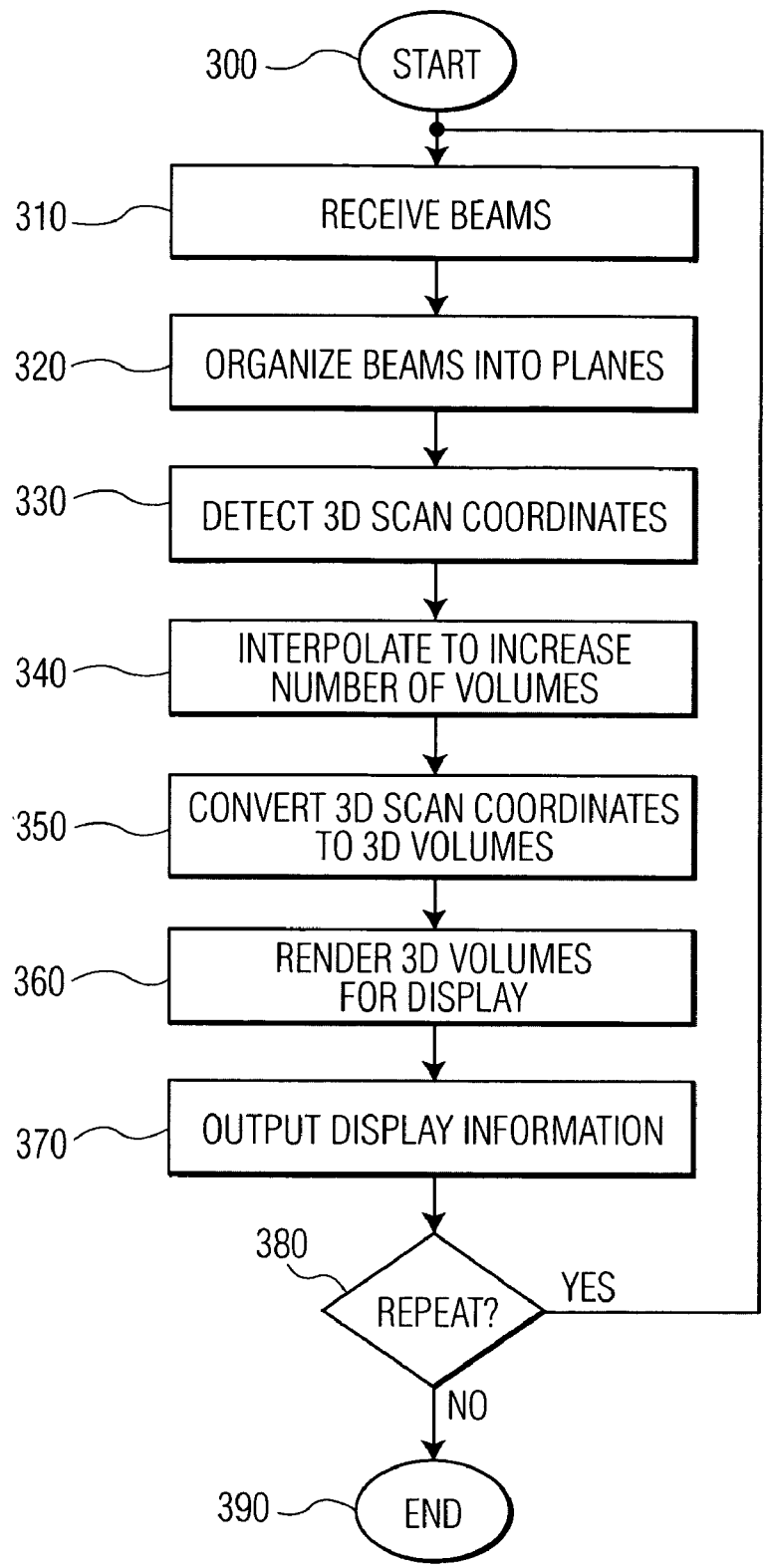
FIG. 4 is another flow chart illustrating a method of producing a high frame rate 3D ultrasound image according to the invention.

FIG. 4 is a flow chart of another exemplary process of applying the invention. The process starts at start 300 and continues to receive beams 310. In receive beams 310, reflected ultrasound frequency beams are received by the process as raw data. The method then continues to organize beams into planes 320.

Organize beams into planes 320 is where the raw data is organized into two-dimensional planes. The process then continues to detect 3D scan coordinates 330. In detect 3D scan coordinates 330, the planes of data are then analyzed to detect any 3D scan coordinates that may exist within the data. The process then continues to interpolate to increase the number of volumes 340.

In interpolate to increase the number of volumes 340, an interpolator can do a straight-line interpolation of the two-dimensional volumes across various iterations of the data in the time dimension. Thus, more two-dimensional volumes are created than were originally detected in the time realm. Thus, an increased frame rate can be displayed. The process then continues to convert 3D scan coordinates to 3D volumes 350. In convert 3D scan coordinates to 3D volumes 350, the process organizes the series of 3D scan coordinates and converts them into 3D volumes. The method then continues to render 3D volumes for display 360.

In render 3D volumes for display 360, the three-dimensional volumes are rendered for display on the display panel. The method then continues to output display information 370. An output display information 370, the render three-dimensional volumes are output to the display device. The method then continues to the determination of repeating 380. In determination of repeat 380, if the method is to continue the method jumps back to receive beams 310. If the method is to conclude the method continues to end 390.

Figure 5:
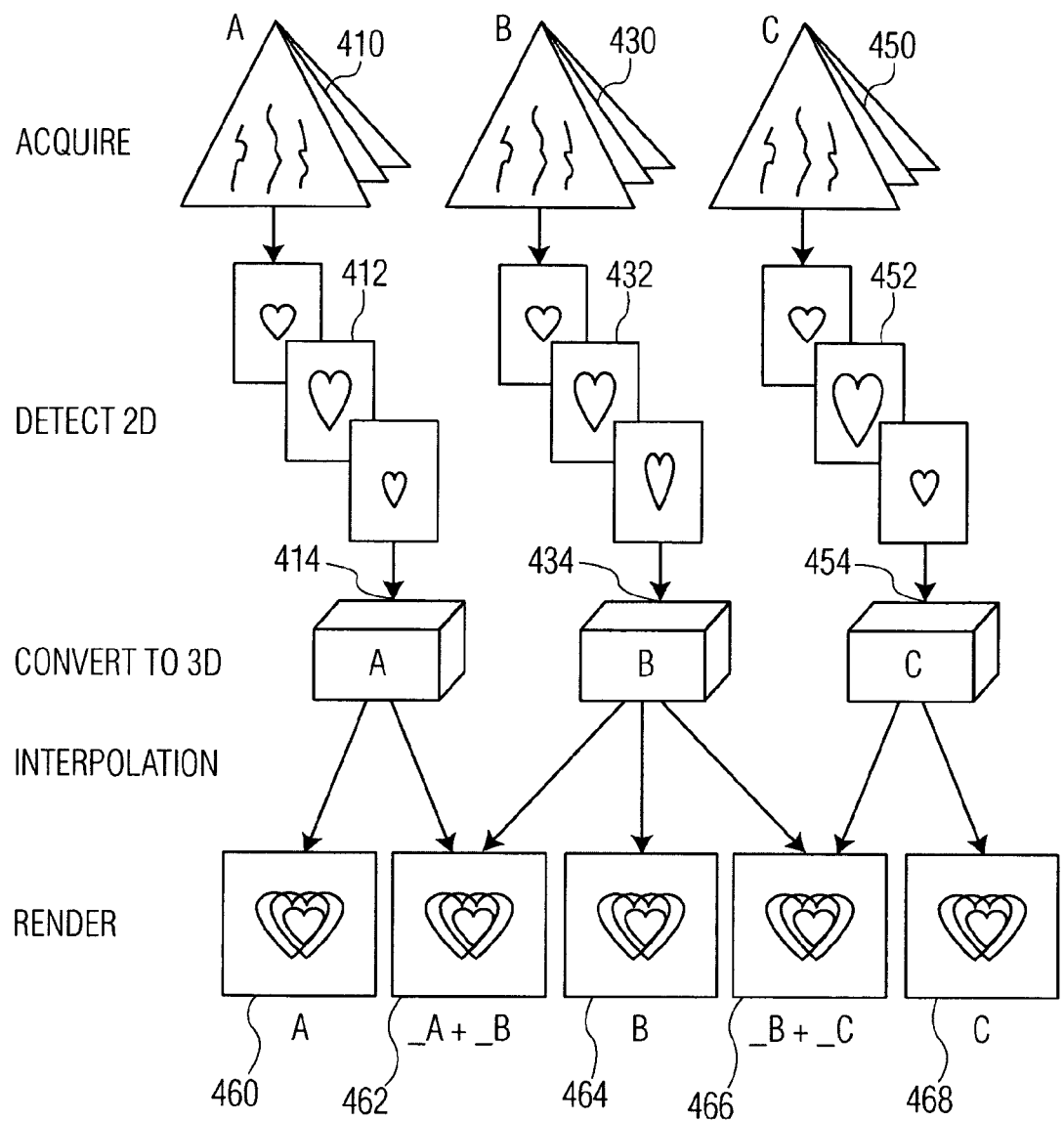
FIG. 5 is an exemplary embodiment of the data that is handled at various stages in the production of a three dimensional ultrasound image.

FIG. 5 is a block diagram showing the data in the process of producing a three-dimensional ultrasound image. The process begins with acquiring images A 410, image B 430 and image C 450 from the raw ultrasound waves that are returned to the ultrasound receiver. The raw data images A 410, image B 430 and image C 450 can be saved in a memory and retrieved at later periods of time.

Next, 2D images can be detected such as images 412, images 432 and images 452. The images then represent two-dimensional slices of the object at an angle, position and time period. The two-dimensional images can then be converted into three-dimensional images to give a block of three-dimensional images A414, a block of three-dimensional images B434 and a block of three-dimensional images C454.

Interpolation can then occur. The interpolation can be any one of several types. The first exemplary type of interpolation is the image itself A 460, half of the image A combined with one half of image B 462, then image B 464. The images can then be rendered to come up with image A460, half image A, plus half image B462, image B464, half image B, plus half image C466 and image C468. Thus, with very little additional computational complexity, a three-dimensional ultrasound device can produce a high frame rate ultrasound image.

Figure 6:
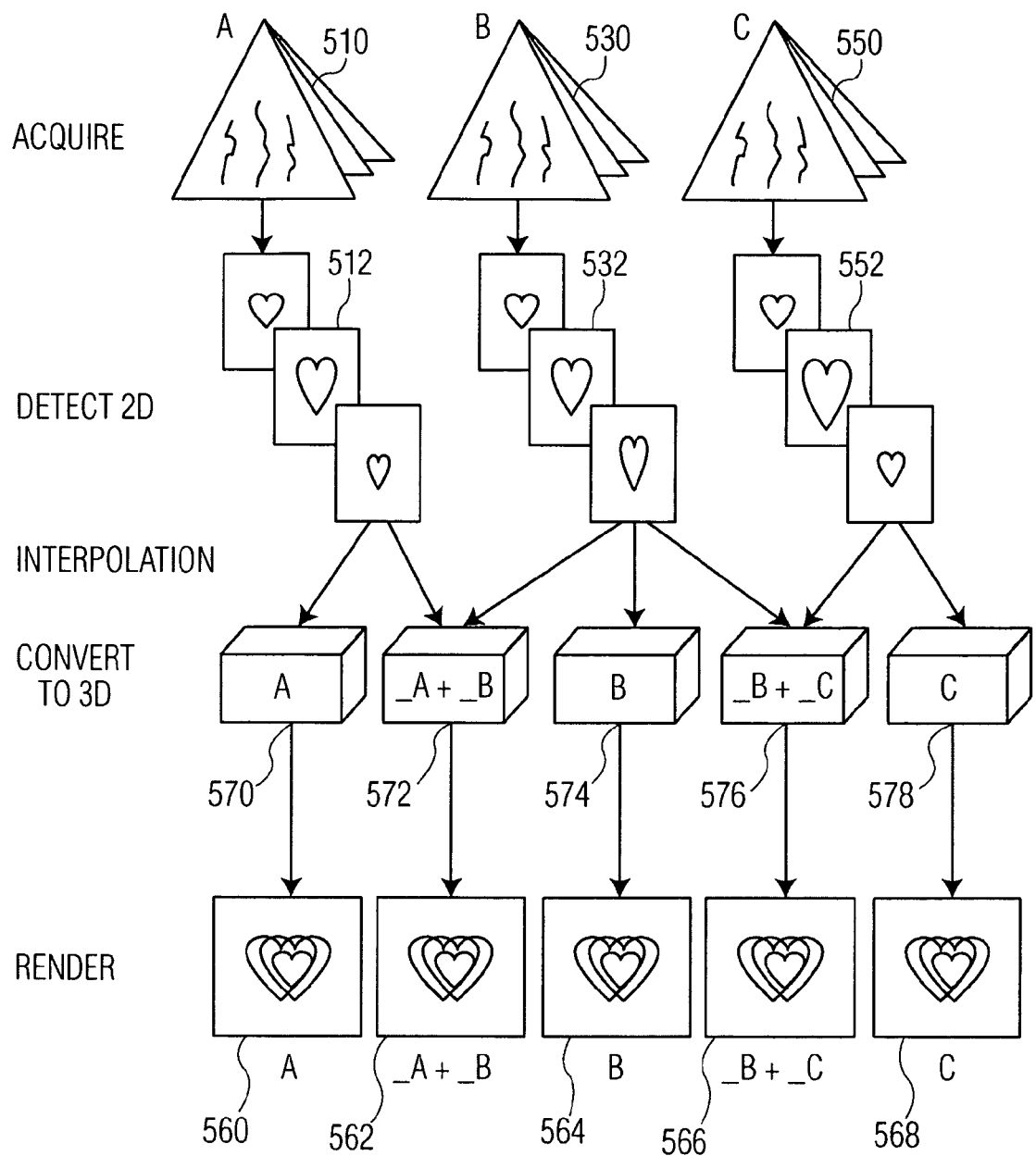
FIG. 6 is another exemplary embodiment of the data that is handled at various stages in the production of a three dimensional ultrasound image.

FIG. 6 is another block diagram showing the data in the process of producing a three-dimensional ultrasound image. The process begins with acquiring images A 500, image B 530 and image C 550 from the raw ultrasound waves that are returned to the ultrasound receiver. The raw data images A 510, image B 530 and image C 550 can be saved in a memory and retrieved at later periods of time.

Next, 2D images can be detected such as images 512, images 532 and images 552. The images then represent two-dimensional slices of the object at an angle, position and time period. Interpolation can then occur. The interpolation can be any one of several types. The first exemplary type of interpolation is the image itself A 570, half of the image A combined with one half of image B 572, then image B 574.

The images can then be converted into three-dimensional images to come up with image A570, half image A, plus half image B572, image B574, half image B, plus half image C576 and image C578. Thus, with very little additional computational complexity, a three-dimensional ultrasound device can produce a high frame rate ultrasound image. The three-dimensional images can then be rendered to give a block of three-dimensional images 560, 562, 564, 566 and 568.

Figure 7:
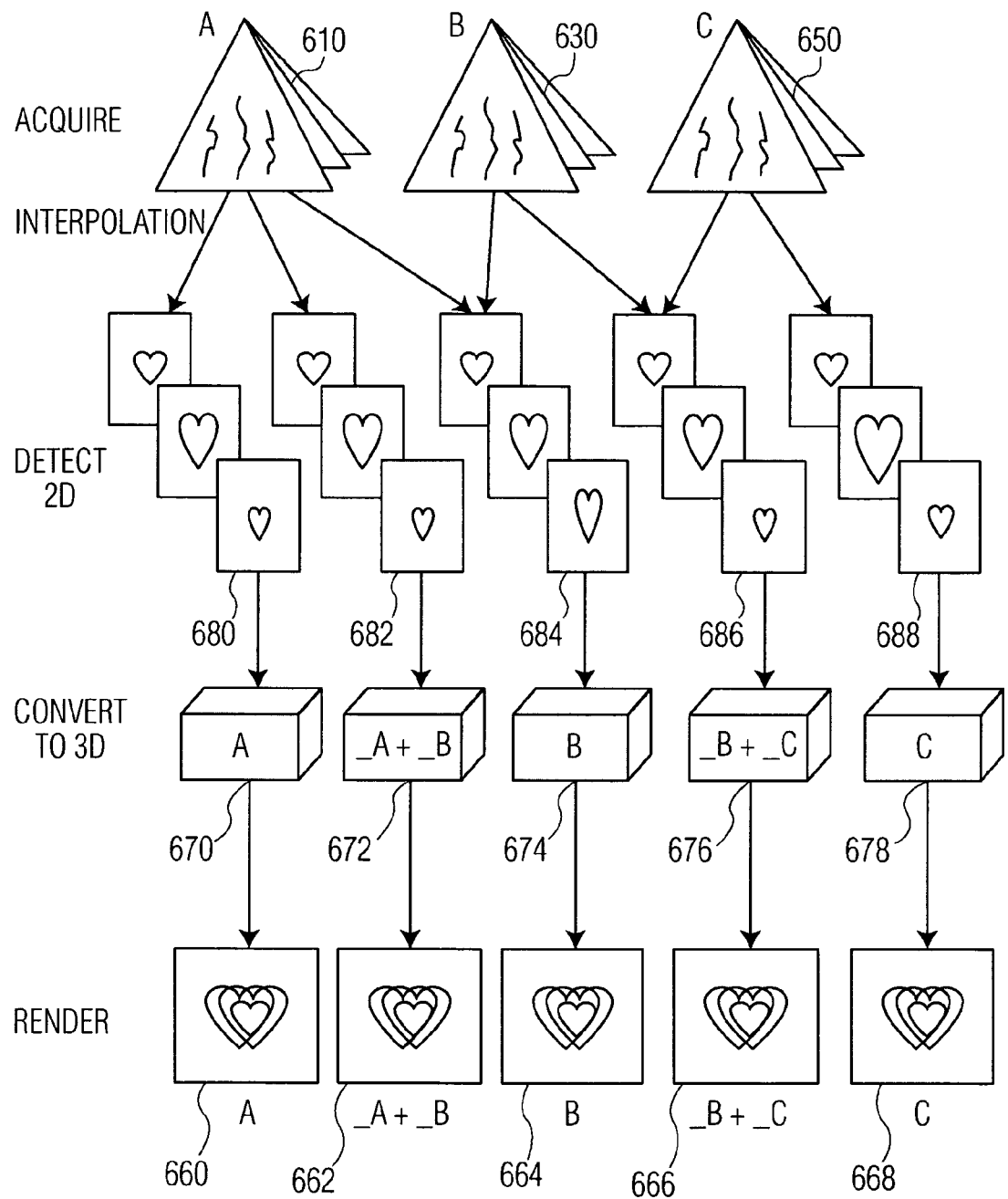
FIG. 7 is a third exemplary embodiment of the data that is handled at various stages in the production of a three dimensional ultrasound image.

FIG. 7 is a block diagram showing the data in the process of producing a three-dimensional ultrasound image. The process begins with acquiring images A 610, image B 630 and image C 650 from the raw ultrasound waves that are returned to the ultrasound receiver. The raw data images A 610, image B 630 and image C 650 can be saved in a memory and retrieved at later periods of time.

Interpolation can then occur. The interpolation can be any one of several types. The first exemplary type of interpolation is the image itself A 680, half of the image A combined with one half of image B 682, then image B 684. The images can then be rendered to come up with image A 680, half image A, plus half image B 682, image B 684, half image B, plus half image C 686 and image C 688.

Next, 2D images can be detected such as images 680, images 682, images 684, images 686 and images 688. The images then represent two-dimensional slices of the object at an angle, position and time period. The two-dimensional images can then be converted into three-dimensional images to give a block of three-dimensional images A 670, a block of three-dimensional images half image A, plus half image B 672, a block of three-dimensional images B 674, a block of three-dimensional images half image B, plus half image C 676 and a block of three-dimensional images C678.

The images can then be rendered, producing images 660, 662, 664, 666 and 668. Thus, with very little additional computational complexity, a three-dimensional ultrasound device can produce a high frame rate ultrasound image. Thus, a lower error rate involved with interpolation early in the process can be balanced by additional complexity involved in handling a larger number of images.

Figure 8:
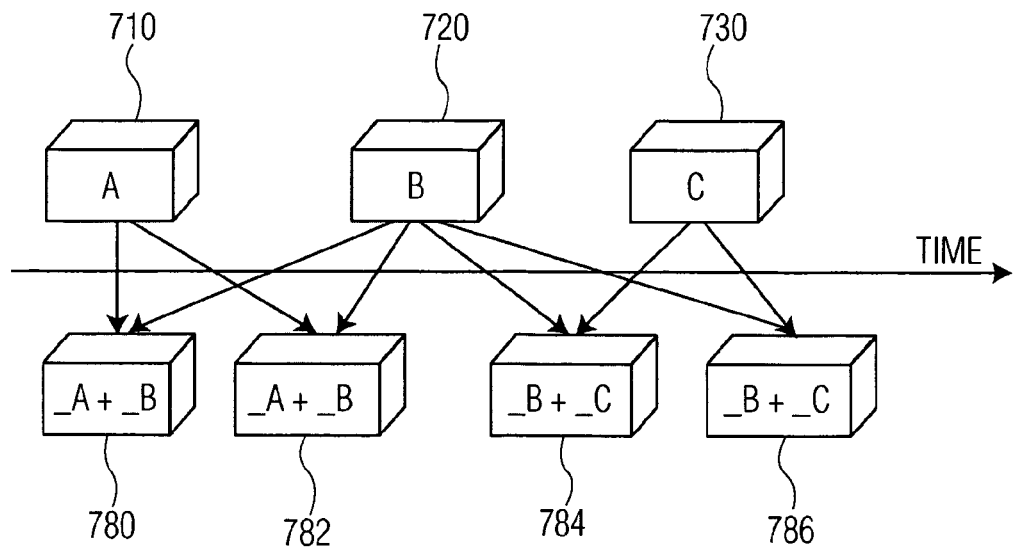
FIG. 8 is an exemplary embodiment of a method for up sampling ultrasound image data.

FIG. 8 is an exemplary embodiment of a second type of interpolation that may be used. In FIG. 8, three-dimensional image A 710, three-dimensional image B 720 and three-dimensional image C 730 can be interpolated into 3-quarters image A plus 1-quarter image B 780, 1-quarter image A plus 3-quarters image B 782, and 3-quarters image B plus 1-quarter image C 784 and 1-quarter image B and 3-quarters image C 786.

Figure 9:
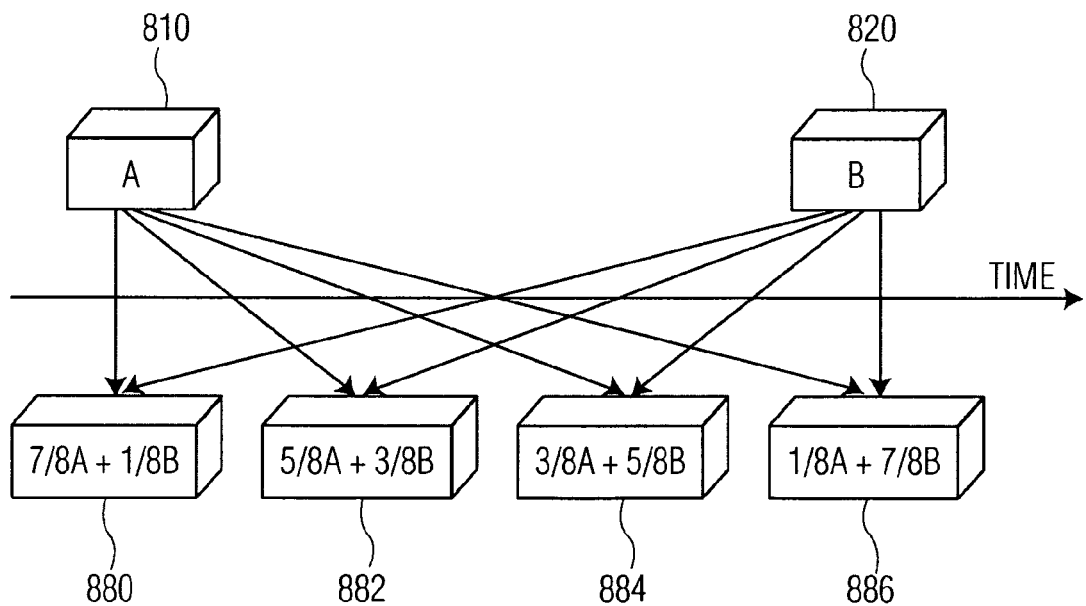
FIG. 9 is another exemplary embodiment of a method for up sampling ultrasound data.

FIG. 9 is another exemplary embodiment of a type of interpolation that may be used. In FIG. 9, three-dimensional image 810 and three-dimensional image C820 can be interpolated into ⅞ image A plus ⅛ image B 880, ⅝ image A plus ⅜ image B 882, ⅜ image A plus ⅝ image B 884 and ⅛ image A plus ⅞ image B 886.

Thus, as can be seen in FIGS. 8 and 9, various other interpolation schemes may be used, as is well known in the art. Various exemplary embodiments have been shown that include differing numbers of beginning and ending frames. Various additional exemplary embodiments include greater or lesser numbers of beginning frames and greater or lesser numbers of ending frames. In addition, the exemplary interpolation has been shown where only two frames are interpolated into the additional frames desired. Additional numbers of frames can be used to produce the interpolated information.

The exemplary embodiments shown also use straight-line interpolation. Various other exemplary embodiments may use various other forms of interpolation such as parabolic, stepped, cubic, FIR (Finite Impulse Response, IIR (Infinite Impulse Response), or other formulaic methods of interpolation.

Thus a person of ordinary skill in the art can appreciate that the present invention may be applied to any type of ultrasound device. Further, the present invention may be retrofitted onto existing ultrasound devices and may expand the number of uses for an ultrasound device because of the additional utility.

Although preferred embodiments of the present invention have been shown and described, it would be appreciated by those skilled in the art that changes may be made in this embodiment without departing from the principles and spirit of the invention, the scope of which is defined in the claims, drawings and their equivalents.

The invention claimed is:

1. A three dimensional ultrasound imaging device, comprising:
    an interpolator that interpolates three-dimensional ultrasound image data corresponding to at least two sequential detected images in an image data stream to obtain at least one interpolated three-dimensional volume, providing up sampled three-dimensional volumes in a time dimension for increasing frame rate.

2. The ultrasound imaging device of claim 1, further comprising:
    a probe that sends ultrasound waves, gathers reflected ultrasound waves and creates the ultrasound image data; and
    a processor that converts the ultrasound image data to the three-dimensional volumes.

3. The ultrasound imaging device of claim 1, further comprising:
    a display that displays the up sampled three-dimensional volumes.

4. The ultrasound imaging device of claim 1, wherein the interpolation comprises at least one of interpolating ultrasound-image data corresponding to 2 sequential detected images to 4 three-dimensional volumes, interpolating ultrasound-image data corresponding to 3 sequential detected images to 4 three-dimensional volumes and interpolating ultrasound-image data corresponding to 3 sequential detected images to 5 three-dimensional volumes.

5. The ultrasound imaging device of claim 1, wherein the interpolation comprises at least one of straight line, parabolic, stepped, cubic, FIR (Finite Impulse Response) and IIR (Infinite Impulse Response) interpolation.

6. The ultrasound imaging device of claim 1, wherein the interpolation comprises interpolating ultrasound-image data corresponding to 2 sequential detected images to 3 three-dimensional volumes.

7. A method of processing ultrasound imaging data, comprising:
    creating up sampled ultrasound image three-dimensional volumes in a time dimension from a plurality of three-dimensional volumes using interpolation;
    storing at least one of the three-dimensional volumes and the up sampled ultrasound image three-dimensional volumes; and
    rendering the up sampled ultrasound image three-dimensional volumes into display data,
    wherein creating the up sampled ultrasound image three-dimensional volumes comprises interpolating three-dimensional ultrasound image data corresponding to at least two sequential detected images to obtain at least one interpolated three-dimensional volume.

8. The method of processing ultrasound imaging data of claim 7, further comprising:
    sending ultrasound waves, gathering reflected ultrasound waves and creating raw ultrasound data; and
    converting the raw ultrasound data to the plurality of three-dimensional volumes.

9. The method of processing ultrasound imaging data of claim 7, further comprising:
    displaying the rendered display data.

10. The method of processing ultrasound imaging data of claim 7, wherein interpolating the plurality of three-dimensional volumes comprises at least one of interpolating ultrasound-image data corresponding to 2 sequential detected images to 4 three-dimensional volumes, interpolating ultrasound-image data corresponding to 3 sequential detected images to 4 three-dimensional volumes and interpolating ultrasound-image data corresponding to 3 sequential detected images to 5 three-dimensional volumes.

11. The method of processing ultrasound imaging data of claim 7, wherein interpolating the plurality of three-dimensional volumes comprises at least one of straight line, parabolic, stepped, cubic, FIR (Finite Impulse Response) and IIR (Infinite Impulse Response) interpolation.

12. The method of processing ultrasound imaging data of claim 7, wherein interpolating the plurality of three-dimensional volumes comprises interpolating ultrasound-image data corresponding to 2 sequential detected images to 3 three-dimensional volumes.

13. A system for three-dimensional ultrasound imaging, comprising:
   an interpolator that interpolates three-dimensional coordinates of ultrasound image data corresponding to at least two sequential detected images in an image data stream to obtain at least one interpolated three-dimensional object, providing up sampled three-dimensional objects in a time dimension for an increased frame rate; and
   a memory that stores at least one of the three-dimensional ultrasound image data and the up sampled three-dimensional objects.

14. The system for three-dimensional ultrasound imaging of claim 13, further comprising:
   a probe that sends ultrasound waves, gathers reflected ultrasound waves and creates the ultrasound image data; and
   a processor that converts the ultrasound image data to the three-dimensional coordinates.

15. The system for three-dimensional ultrasound imaging of claim 13, further comprising:
   a render engine that renders display data from the up sampled three-dimensional objects; and
   a display device that displays the rendered display data.

16. The system for three-dimensional ultrasound imaging of claim 13, wherein the interpolation comprises at least one of interpolating three-dimensional coordinates corresponding to 2 sequential detected images to 4 three-dimensional objects, interpolating three-dimensional coordinates corresponding to 3 sequential detected images to 4 three-dimensional objects and interpolating three-dimensional coordinates corresponding to 3 sequential detected images to 5 three-dimensional objects.

17. The system for three-dimensional ultrasound imaging of claim 13, wherein the interpolation comprises at least one of straight line, parabolic, stepped, cubic, FIR (Finite Impulse Response) and IIR (Infinite Impulse Response) interpolation.

18. The system for three-dimensional ultrasound imaging of claim 13, wherein the interpolation comprises interpolating three-dimensional coordinates corresponding to 2 sequential detected images to 3 three-dimensional objects.

* * * * *